United States Patent [19]
Higuchi et al.

[11] 3,943,137
[45] Mar. 9, 1976

[54] ACRONYCINE DERIVATIVES

[75] Inventors: Takeru Higuchi; Arnold J. Repta; David W. A. Bourne, all of Lawrence, Kans.

[73] Assignee: University of Kansas Endowment Association, Lawrence, Kans.

[22] Filed: July 9, 1973

[21] Appl. No.: 377,401

[52] U.S. Cl. ............................. 260/279 R; 424/257
[51] Int. Cl.² ........................................ C07D 491/04
[58] Field of Search ............................... 260/279 R

[56] References Cited
UNITED STATES PATENTS

| | | | |
|---|---|---|---|
| 3,673,163 | 6/1972 | Walkling | 260/279 R |
| 3,843,658 | 10/1974 | Smithwick, Jr. | 260/279 R |

OTHER PUBLICATIONS

T. R. Govindachari et al., Tetrahedron 22, 3245 (1966).

*Primary Examiner*—Nicholas S. Rizzo
*Assistant Examiner*—Mark L. Berch
*Attorney, Agent, or Firm*—Bacon & Thomas

[57] ABSTRACT

Acronycine derivatives having the structural formula:

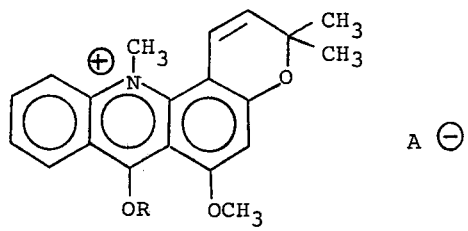

wherein R is acyl and A is an anion of a suitably strong acid, stabilized formulations thereof and pharmaceutical compositions comprised of same exhibit broad spectrum antitumor activity, and are especially suited for intravenous administration.

10 Claims, 1 Drawing Figure

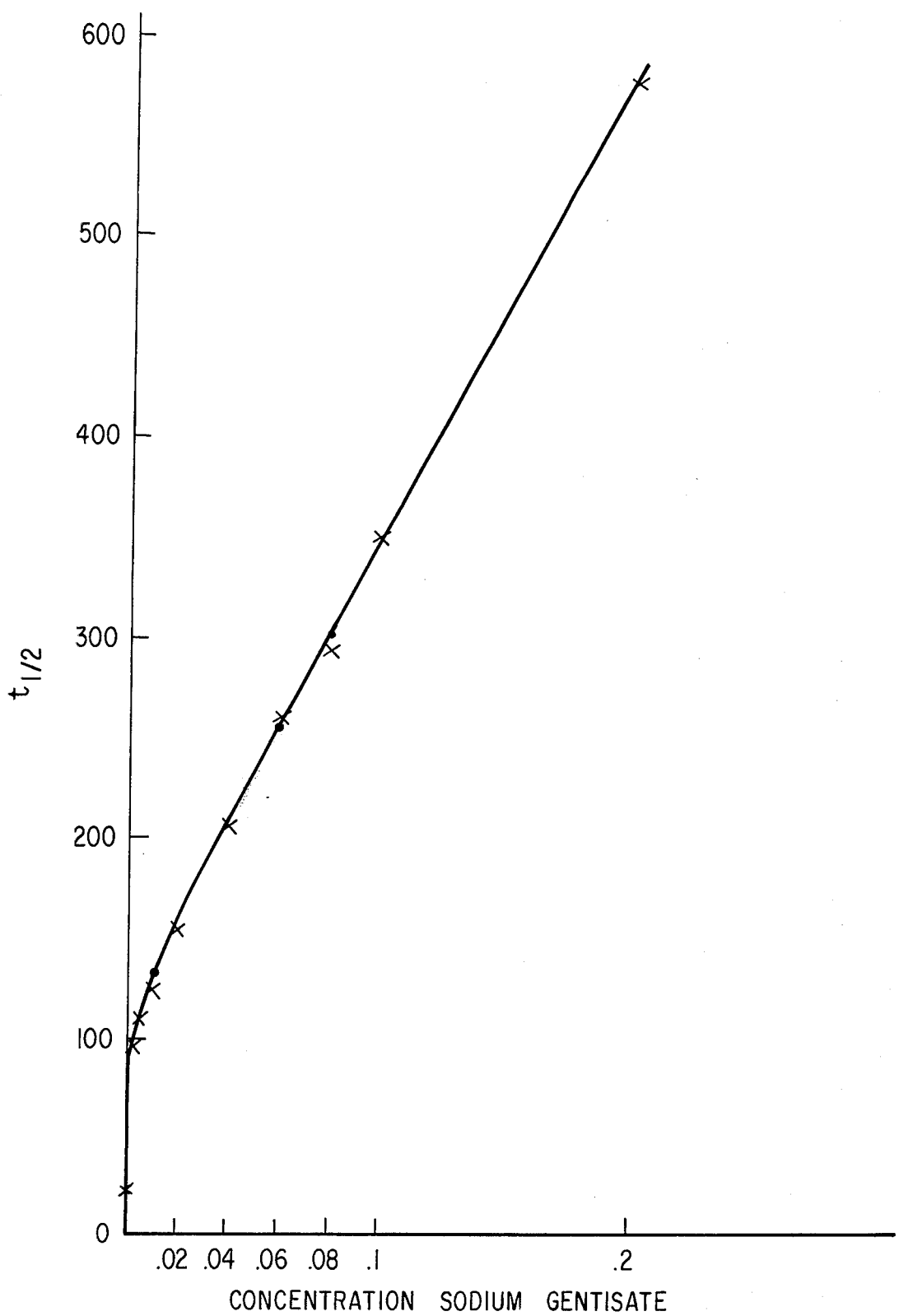

ACRONYCINE DERIVATIVES

The invention described herein was made in the course of work under a grant or award from the Department of Health, Education & Welfare.

BACKGROUND OF THE INVENTION

1. Field of the Invention

This invention relates to novel derivatives of acronycine and to the stabilization of such derivatives by use of suitable complexing agents. These novel derivatives, stable formulations thereof and pharmaceutical compositions comprised of same exhibit broad spectrum antitumor activity and are well suited for intravenous injection.

2. Description of the Prior Art

Svoboda et al, reported at *J. Pharm. Sci.*, 55, pp. 758 – 768 (1966), which is hereby expressly incorporated by reference herein and is relied upon, found that the alkaloid acronycine, an acridone compound isolated from an Australian plant (*Acronychia Baueri* Schott), exhibits a broad antitumor activity. Tested as an

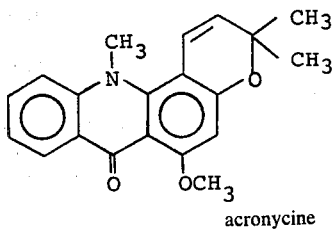

acronycine aqueous suspension, acronycine produced significant reductions in the size of a number of tumors. In the Svoboda laboratory, acronycine has been shown to be a potent antitumor agent against a multiplicity of mouse neoplasms, significant activity having been demonstrated against 12 of 17 tumors tested with a wide range of dose levels. Not only is this alkaloid broad spectrum in character, but it is also effective by various routes of administration and it has demonstrated significant activity in delayed therapy experiments. The oral and subcutaneous activities of this alkaloid are of special interest since most of the clinically proved oncolytic agents presently used are ineffective orally and elicit intolerable side effects when administered subcutaneously.

When tested against the adenocarcinoma 755, C-1498 leukemia, and the X-5563 myeloma, acronycine also displayed significant activity by both the oral and subcutaneous routes. Furthermore, there was no evidence of skin irritation or alopecia when administered subcutaneously.

However, only minimum activity was observed when this alkaloid was administered intraveneously. This was attributed to its insolubility (2–3 mg/liter), making effective clinical evaluation of this drug very difficult, sufficiently high blood levels not being attained. In fact, in several instances blockage of the circulatory system was evidenced, autopsy revealing an actual aortic block by the compound itself. One attempt at solubilizing the subject alkaloid involved coprecipitating the drug with polyvinyl-pyrrolidone (PVP); this produced only a fifteenfold increase in solubility but also an increase in antitumor activity, thus indicating that the low solubility is causing a decrease in such activity. Compare Svoboda et al, *J. Pharm. Sci.*, 60, 333 (1971), also expressly incorporated by reference herein and relied upon.

It will thus be seen, clinical testing of acronycine having been effectively limited to the oral dosage, subcutaneous and intraperitoneal forms, that the extremely low solubility of acronycine results in marginal absorption when administered intravenously and, therefore, minimal bioavailability. Accordingly, the chemotherapeutic management of the various tumors and neoplasms being best effected by means of suitable parenteral or intravenous solution, serious need exists for a pro-drug form of acronycine which avoids the aforesaid problems of absorption and related problems of bioavailability.

SUMMARY OF THE INVENTION

Accordingly, it is a primary object of this invention to provide certain novel derivatives of acronycine which can be readily synthesized and which are much better suited than the acronycine free base for pharmaceutical use because of the greatly enhanced solubility of such derivatives.

Another object of this invention is to provide certain novel derivatives of acronycine useful in the chemotherapeutic management of the various tumors and neoplasms.

Still another object of the invention is to provide certain acronycine derivatives well suited for intravenous administration.

Another object is to provide such derivatives which avoid the art recognized problems of absorption and minimal bioavailability associated with the free base thereof.

Yet another object of this invention is to provide a pro-drug form of acronycine which is effectively up to a hundredfold more soluble than acronycine and which, upon administration, reverts to the free base drug within a matter of minutes.

Still another object of the invention is the stabilization of certain novel derivatives of acronycine by complexation with certain suitable complexing agents.

Still another object is a stable and suitable formulation of a pro-drug form of acronycine.

Another object of this invention is to provide a hydrolysis resistant formulation of a pro-drug form of acronycine to increase the stability of pharmaceutical solutions comprised thereof prior to their parenteral administration.

In attaining the objects of this invention, one feature resides in the provision of certain acronycine derivatives having the structural formula:

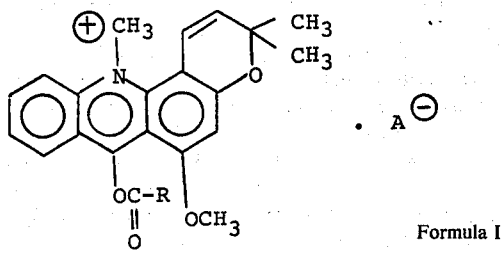

Formula I wherein R is substituted or unsubstituted, straight or branched chain lower alkyl having from 1 to 8 carbon atoms, substituted or unsubstituted aryl having from 6 to 10 carbon atoms, e.g., phenyl and naphthyl, substituted or unsubstituted aralkyl and alkaryl wherein the alkyl and aryl moieties are as defined above, or such other moiety that when the resulting derivatives of the Formula I are subjected to conditions of hydrolysis, either in vitro or in vivo, same revert to the acronycine free base form. Exemplary of the ester groups of the derivatives of the Formula I comprising the moiety R, the acetate, propionate, isobutyrate, pivalate and trifluoroacetate are representative. "A" is any anion of a suitably strong acid, advantageously the perchlorate, chloride, sulfate, phosphate, bromide or methanesulfonate. Alternatively, "A" may be the anion of any one of those complexing agents characterized, infra.

Another feature of this invention resides in the stabilization of the aforesaid pro-drug forms of acronycine by complexation with a suitable complexing agent to increase the stability of pharmaceutical solutions thereof prior to their parenteral administration. Suitable complexing agents include the organic acids, preferably the cyclic and aromatic organic acids, and most preferably the hydroxy aromatic acids. Representative of such organic acids are gentisic, gamma-resorcyclic, p-hydroxycinnamic, 2-furoic, m-hydroxycinnamic, 3,4-dimethylcinnamic and 3-methylgentisic. Also representative are the alkali metal salts of the aforesaid organic acids, e.g., sodium gentisate, sodium gamma-resorcylate, sodium p-hydroxycinnamate, sodium 2-furoate, sodium m-hydroxycinnamate, sodium 3,4-dimethylcinnamate and sodium 3-methylgentisate.

Other objects, features and advantages of this invention will become more apparent from the description which follows.

BRIEF DESCRIPTION OF THE DRAWING

The FIGURE of drawing is a rate of hydrolysis plot of half-life of a labile ester according to the invention, stabilized with sodium gentisate, versus sodium gentisate concentration.

DETAILED DESCRIPTION OF THE INVENTION

Acronycine, as heretofore mentioned, has been shown to have significant antitumor activity in various screening systems; Svoboda et al, *J. Pharm. Sci.*, supra. However, the clinical testing of this drug has been severely hampered by the low solubility of the acronycine free base in, and concomitant minimal bioavailability from, aqueous media. Acronycine's solubility is only about 2–3 mg per liter of water. It has not been discovered by the inventors that increased water solubility of acronycine results by synthesizing various pro-drug derivatives thereof. These pro-drug derivatives are carbonyl acylated quaternary forms of acronycine and are much more soluble (greater than fiftyfold more soluble and even up to and greater than a hundredfold more soluble) than the acronycine free base. Upon introduction of the pro-drugs of this invention into an aqueous solvent, same dissolve rapidly and undergo rapid hydrolysis to yield the parent acronycine. And even upon intravenous injection, same revert to the parent drug in a matter of minutes. From a consideration of the chemistry of the acronycine molecule, it was discovered that if a charge is introduced into the molecule via quaternization thereof, its solubility was increased. With compounds of higher $pK_a$'s, a formulation with a lower pH is often possible. But since acronycine has a $pK_a$ of about 1.6, a solution of the quaternary salt would be too highly acidic for I.V. formulation. On the other hand, by synthesizing a slowly hydrolyzing derivative of the salt, a positive charge could be conferred on the molecule over all pH ranges. The products of esterification of the carbonyl oxygen have been found to be admirably well suited for this purpose. These esters are formed on the oxygen at the 9 position on the molecule and hold the structure with a positive charge on the nitrogen. And this positive charge is lost only upon hydrolysis of the ester link. Because of the higher $pK_a$ of acronycine, the aforesaid O-acylation of the quaternary salts of acronycine under acid conditions proceeds very readily.

Quaternization of the acronycine free base can be effected simply by precipitation by the required acid from a suitable solvent. For example, the acronycine is converted to any suitable salt (including the perchlorate, chloride, sulfate, and any other salt of a strong acid) by dissolving the same in, e.g., acetone and adding an excess molar quantity of the respective acid. The acronycinium salt which forms is readily precipitated, removed by filtration, and dried.

The esters of the Formula I are prepared by reacting the acronycinium salt with any desired suitable acylating agent (such as the acid anhydride or acid chloride of, e.g., the acids acetic, propionic, isobutyric, pivalic, trifluoroacetic, and others) at elevated temperatures for the required period of time. The reaction mixture is next cooled, filtered to remove unreacted solid material, and then diluted with, e.g., diethyl ether. The precipitate which forms is separated by filtering, washed with ether, and dried. The solids obtained contain about 50% to about 80% of the desired acylacronycinium salt.

The anion of the acid used presumably acts as a catalyst for the subsequent acylation according to the following reaction scheme:

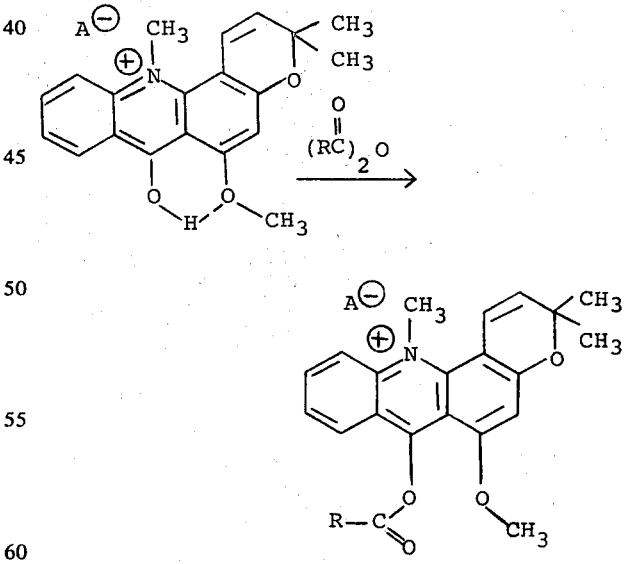

A comparison of some of the physical properties of the base, perchlorate salt, and acetate ester is of interest. The wavelength maximum in the visible range for the base, salt and ester, respectively, is 395, 455, 510 nm., giving a yellow, orange, and purple color to the compounds. The base is soluble in acetone and benzene, insoluble in water. The salt is soluble in water and insoluble in acetone and benzene. The ester is found to be insoluble in benzene, but soluble in water and acetone. Acetyl acronycinium perchlorate moreover has a solubility in water of 250 mg/liter (i.e., a hundredfold increase in solubility over the free base). NMR, IR and elemental analysis confirm synthesis of the ester. By following the reaction spectrophotometrically at 510 nm., the ester was shown to follow first order kinetics with a half-like of 20 to 25 minutes at 25°C. in neutral pH. This rate was remarkably insensitive to ionic strength, pH (below 8–9), anion, ester group size (e.g., acetate, propionate, isobutyrate, pivalate, etc.). However, the rate was greatly increased with increasing dielectric constant. This evidence suggested then that the hydrolysis was proceeding via a $S_{N_1}$ mechanism. Temperature also had a marked effect on the rate of hydrolysis, as a determined enthalpy of activation of about 20 kcal/mole indicates.

In studying the kinetics of hydrolysis of the aforesaid quaternary acyl acronycinium salts to yield acronycine, it was determined that the increased solubility and the rapid rate of hydrolysis were such that said quaternary derivatives were eminently well suited for use as pro-drugs. Nevertheless, the facility with which hydrolysis occurred in water presented one problem of too rapid precipitation from solution as a consequence of the formation of the slightly soluble acronycine free base. In order to prevent any objectionable hydrolysis of the pro-drug in aqueous solution prior to administration, it was discovered that the hydrolytic rate thereof could be retarded by the formation of intermolecular complexes therewith. Utilizing suitable complexing agents to form intermolecular complexes with the pro-drug and thereby retard the hydrolytic reaction was found to markedly increase the stability of the carbonyl acylated quaternary derivatives of the Formula I in solution. It was also found that this approach resulted in solutions in which the half-life of hydrolysis of the pro-drug was increased from about 20 minutes in water alone to about 8 or more hours in water containing a sufficient quantity of suitable ligand. Moreover, since complexation is an equilibrium phenomenon, extensive complexation occurs in the relatively concentrated drug solution. However, upon dilution with aqueous media such as body fluids, the complex species dissociates, and the pro-drug is then rapidly hydrolyzed to the desired drug species, namely, the acronycine free base. Exemplary of the complexing agents which can be used in aqueous solutions of the acylacronycinium salts to retard the hydrolysis thereof are a wide variety of the organic acids and alkali metal salts thereof, preferably the cyclic and aromatic organic acids, and most preferably the hydroxy aromatic acids. Representative of same are gentisic acid, gamma-resorcylic acid, p-hydroxycinnamic acid, 2-furoic acid, m-hydroxycinnamic acid, 3,4-dimethylcinnamic acid and 3-methylgentisic acid, and the sodium and other salts thereof. A suitably stable and useful formulation of an acylacronycinium salt for use in the preparation of pharmaceutical solutions can be simply made by preparing a powder mixture of the desired acylacronycinium salt and a suitable complexing agent in such proportions and amounts that upon addition of an aqueous solvent, the resulting solution would be of a composition such that the hydrolysis of the acylacronycinium salt would be greatly retarded.

Among the number of the hydroxy aromatic acids, particularly the hydroxy benzoic acids that have been utilized according to the invention, excellent results have been attained with the preferred 2,5-dihydroxybenzoic acid (gentisic acid). Employing the acetyl acronycinium perchlorate salt and the sodium salt of such preferred acid, it can be seen from the plot of the FIGURE of drawing of half-life vs. sodium gentisate concentration that the rate of hydrolysis of the acylacronycinium salt was greatly reduced. Mathematical analysis of the results dictates describing this system by two equilibria; one to one complex and one to two complex formation (one drug and two ligand), with the 1:1 complex and the free drug hydrolyzing with half-lives of 120 and 23 minutes, respectively. The solid curve of the FIGURE of drawing illustrates the result of such model. Constants required for the $t_{1/2}$ calculations were as follows:

$K_{1:1} = 4,081$ $K_{1:2} = 80,000$ $t_{1/2}$ Free Drug = 23 min.

$t_{1/2}$ 1:1 Complex = 119 min.

$t_{1/2}$ 1:2 Complex = ∞ and the experimental conditions were:

$\mu = 1.0$ M $T = 25.0°C$

Followed at 520 nm.

pH = 6.5

In order to further illustrate the present invention and the advantages thereof, the following specific examples are given, it being understood that the same are intended only as illustrative and no wise limitative.

EXAMPLE 1

Preparation of Acetylacronycinium Perchlorate

Five grams of acronycine were dissolved in 175 mls of acetone. Four mls of concentrated (about 70%) perchloric acid was added slowly. The resulting precipitate, acronycinium perchlorate, was filtered off and dried. The yield was 6.5 g (99%).

One gram of the acronycinium perchlorate was added to 20 mls of acetic anhydride and heated at 100°C. for 20 minutes. The reaction mixture was then cooled and filtered. The filtrate was added to 200 mls of anhydrous diethyl ether and the resulting solid which formed was separated by filtration and dried overnight in a vacuum desiccator at room temperature and a pressure of about 10 mm mercury. The solid obtained contained 80–90% of acetylacronycinium perchlorate and about 10–20% of unreacted acronycinium perchlorate. The sample melted at about 240° C. with decomposition. The NMR and IR spectra were compatible with Formula I where R = acetyl. An elemental analysis was as follows:

| Element | Calculated | Found |
|---------|------------|-------|
| C | 56.96 | 55.8 |
| H | 4.75 | 4.6 |
| N | 3.01 | 3.0 |

Solubility ≃ 25 mg/100 mls of water

Upon standing in aqueous solution, a precipitate formed which was characterized as acronycine by melting point, thin-layer chromatography, and UV spectra.

The solubility of the various acylacronycinium salts varied considerably, depending on (1) the nature of the acyl group and (2) the nature of the anion in the salt.

The hydrolysis of the acylacronycinium salts in aqueous solution was found to be first order and had a half-life of 20–25 minutes at 25° C. It was also found that the rate of hydrolysis was virtually independent of the nature of R, A, ionic strength, and pH over the range of pH = 2–8. An increased rate of hydrolysis was observed at pH > 8.

EXAMPLE 2

Stabilization of Acylacronycinium Salts in Aqueous Media

Use of suitable complexing agents in aqueous solutions of the acylacronycinium salts retarded the hydrolysis of such compounds. Some of the complexing agents used were the following: sodium gentisate, sodium gamma-resorcylate and sodium cinnamate. Table I reflects the effects of sodium gentisate concentration on the apparent rate of hydrolysis of acetylacronycinium perchlorate.

Table I

Apparent half-line of acetylacronycinium perchlorate ($10^{-4}$M) as a function of sodium gentisate concentration in water at 25° C. pH = 6.0.

| Sodium Gentisate Concentration (M/l) | $t_{1/2}$ (min) |
|---|---|
| 0 | 23 |
| $2.5 \times 10^{-3}$ | 93 |
| $5 \times 10^{-3}$ | 108 |
| $1 \times 10^{-2}$ | 125 |
| $2 \times 10^{-2}$ | 156 |
| $4 \times 10^{-2}$ | 207 |
| $6 \times 10^{-2}$ | 260 |
| $8 \times 10^{-2}$ | 295 |
| 0.1 | 350 |
| 0.2 | 578 |

EXAMPLE 3

Complexation of Acylacronycinium Salts

Based on the type of data shown in Table I, a suitably stable and useful formulation of the acylacronycinium salt for use in the preparation of pharmaceutical solutions was made. The approach used consisted of preparing a powder mixture of the acylacronycinium salt and the complexing agent in such proportions and amounts that upon addition of an aqueous solvent, the resulting solution was of a composition such that the hydrolysis of the acylacronycinium salt was greatly retarded.

Experimental: Twenty-five mg of acetylacronycinium perchlorate and 4.6 g of sodium gentisate were powdered, mixed and placed in a suitable vial and sealed. Just prior to use, 100 ml of water was added to the vial, and the solid material dissolved rapidly, yielding a solution which was about $10^{-3}$M with respect to acetylacronycinium perchlorate and about 0.2 Molar with respect to sodium gentisate. Under these conditions, the acetylacronycinium had an apparent hydrolytic half-life of about 9.5 hours.

EXAMPLE 4

Preparation of Trifluoroacetylacronycinium Perchlorate

One gram of acronycinium perchlorate prepared as in Example 1 was refluxed with about 20 mls of trifluoroacetic anhydride. Very little reaction occurred. 10 mls of trifluoroacetic acid were then added to the reaction mixture and reaction occurred within a matter of a few minutes (flash heated with near boiling water). A greenish-brown solution was produced. The reaction mixture was next cooled and filtered. The filtrate was added to 100 mls of diethyl ether and copious, fluffy red purple precipitate was produced which was placed in a desiccator while still quite moist. Some hydrolysis occurred overnight. The sample reacted very quickly with water and methanol; there was little reaction with chloroform (until water was added).

EXAMPLE 5

Preparation of Propionylacronycinium Perchlorate

Duplicating the procedure outlined in Example 4, 500 mg of the acronycinium perchlorate were heated with 10 ml of propionic anhydride at 120°C for 15 to 20 minutes. The reaction mixture was then cooled and filtered. The resultant propionylacronycinium perchlorate provided the following hydrolysis data:

In Phosphate Buffer:
| pH = | 7.50 | k = 0.028 min$^{-1}$ | $t_{1/2}$ = | 24.4 min | r = 0.999 | T = | 25°C |
|---|---|---|---|---|---|---|---|
|  | 7.60 | 0.047 |  | 14.6 | 0.999 |  | 25°C |
|  | 7.60 | 0.046 |  | 14.9 | 0.999 |  | 25°C |

With Gentisic Acid (0.05 M):
| pH = | 2.78 | k = 0.008 min$^{-1}$ | $t_{1/2}$ = | 86.4 min | r = 0.998 | T = | 25°C |
|---|---|---|---|---|---|---|---|
|  | 2.70 | 0.0067 |  | 102.8 | 0.999 |  | 25°C |

EXAMPLE 6

Preparation of Pivalylacronycinium Perchlorate

Duplicating the procedure outlined in Example 4, 20 mg of the acronycinium perchlorate were heated with 0.5 ml of pivalylchloride in a sealed ampoule in a stirred oil bath, at 90° C. The reaction was repeated with pivalyl anhydride. The pivalylacronycinium perchlorate resultant product was hydrolyzed in phosphate buffer at 25° C. and the following data was generated:

| $r^2$ = 0.9984 | k = 0.043 min$^{-1}$ | $t_{1/2}$ = 16.06 min |
|---|---|---|
| 0.9990 | 0.0387 | 17.91 |
| 0.9990 | 0.0289 | 23.98 |

EXAMPLE 7

Preparation of Isobutyrylacronycinium Perchlorate

Duplicating the procedure of Example 4, 500 mg of the acronycinium perchlorate were heated with 10 ml isobutyric anhydride in a test tube at 130°–135° C. 10 further ml of isobutyric anhydride were added. The reaction was cooled, filtered and precipitated with diethyl ether. In phosphate buffer, at pH 6.33 and 24° C., k = 0.02057 min$^{-1}$, $t_{1/2}$ = 33.7 min and r = 0.99967.

EXAMPLE 8

Preparation of Acetylacronycinium Sulfate

Acronycinium sulfate was prepared according to the procedure of Example 1, utilizing sulfuric acid, and 500 mg thereof were heated with 10 ml acetic anhydride over boiling water. The reaction mixture was cooled, filtered and 8 ml thereof were precipitated with diethyl ether. The following data of hydrolysis were generated:

In Phosphate Buffer (25° C.):
| | | |
|---|---|---|
| $t_{1/2}$ = 19.3 min. | $r^2$ = 0.9997 | k = 0.000600 sec$^{-1}$ |
| 19.7 | 0.9995 | 0.000586 |
| 21.5 | 0.9999 | 0.000538 |

In Acetate Buffer (25° C.):
| | | |
|---|---|---|
| $t_{1/2}$ = 26.5 | $r^2$ = 0.9998 | k = 0.000436 sec$^{-1}$ |
| 27.3 | 0.9994 | 0.000423 |

EXAMPLE 9

Preparation of Acetylacronycinium Chloride

Acronycinium chloride was prepared according to the procedure of Example 1, utilizing hydrochloric acid, and 300 mg thereof were first heated to 100° C. and then were reacted with 5 ml acetic anhydride. The reaction was complete in less than one minute and the reaction mixture was cooled, filtered and one ml thereof was precipitated with diethyl ether. The precipitate was essentially red-purple in color. The following data of hydrolysis were generated:

In Methanol/Water (90/10):
| | | | |
|---|---|---|---|
| pH = 1.28 | k = 0.000417 sec$^{-1}$ | $t_{1/2}$ = 27.7 min | $r^2$ = 0.9997 |
| 0.28 | 0.000413 | 28.0 | 0.9997 |

EXAMPLE 10

Complexation of Acetate-Chloride 300 mg acetylacronycinium chloride were dissolved in 10 ml of ice cold water, shaken, and filtered into 20 ml of ice cold sodium gentisate (1 M), and into 20 ml of ice cold gentisic acid, respectively. The precipitates were filtered off, dried with a vacuum pump and stored in an evacuated desiccator. The precipitate was more abundant from the sodium gentisate solution.

EXAMPLE 11

Complexation of Acetate-Perchlorate

Acetylacronycinium perchlorate prepared as in Example 1 was complexed with gamma-resorcylic acid, cinnamic acid, p-hydroxycinnamic acid and 3,4-dihydroxycinnamic acid, respectively, by duplicating the procedure of Example 10. $t_{1/2}$ and kmin$^{-1}$ data for the respective samples, at pH 6.5, 25° C. in 0.05 M phosphate buffer, were roughly comparable to those generated with the sodium gentisate complex.

The known broad spectrum antitumor activity of acronycine against a multiplicity of mouse neoplasms has also been demonstrated with respect to the acylacronycinium salts of the Formula I, as well as with respect to the stable, complex, formulations thereof. The methodology used for mammalian organism tumor testing of the pro-drug derivatives of this invention, including the stabilized complexed esters, and even the quaternized intermediates, per se, is described at Johnson et al., *J. Cancer Res.*, 20, 1016 (1960), and essentially consists of subcutaneous trocar implantation of solid tumors in the axillary region and intraperitoneal inoculation of ascitic and leukemic cells with standard cell inocula. The three systems of choice for assaying the activity of the pro-drugs of this invention, including their complexation forms, are the C-1498 myelogenous leukemia, the X-5563 plasms cell myeloma, and AC-755. Treatment is usually initiated 24 hr. after implantation, exception being made in the case of the X-5563 myeloma, in which case treatment was initiated 3 days after transplantation.

When tested on mice against the adenocarcinoma 755, C-1498 leukemia, and the X-5563 myeloma, in the dosage range reported by Svoboda et al, *J. Pharm. Sci.*, 55, supra, and utilizing the intraperitoneal, intravenous and subcutaneous routes of administration, a freshly prepared aqueous solution containing acetylacronycinium perchlorate (6 × 10$^{-4}$ M) and sodium gentisate (0.2 M) displayed not only that same significant activity therein defined and reported in Tables II, III, IV, V, VI, VII and X of Svoboda et al. by both the intraperitoneal and subcutaneous routes, but also substantially identically significant activity was even observed when the solution was administered intravenously. This in contradistinction to the "only minimum activity" observed by Svoboda et al. when the free base alkaloid was administered intravenously. For the testing, a regimen of a single dose per day of the acetylacronycinium perchlorate-sodium gentisate solution, for a period of 9–10 consecutive days, was employed.

Moreover, as each of the quaternary intermediates, the carbonyl acylated forms thereof of the Formula I, and the complexation products of such esters, all in accordance with this invention are true pro-drugs, namely, pharmaceutically acceptable derivatives which in vivo or in vitro revert to the parent molecule, in this instance the acronycine free base, each would be expected to and in fact does display the same antitumor activity reported by Svoboda et al. against the 12 of 17 experimental mouse neoplasms.

Thus, this invention provides various pharmaceutically acceptable pro-drug forms of acronycine which are significantly more soluble than the acronycine of commerce, which are significantly better absorbed than said acronycine, especially when formulated as a stabilized parenteral solution suitable for intravenous injection, which are significantly more bioavailable than said acronycine, and which open another avenue in the chemotherapeutic management of mammalian organism tumors and neoplasms.

While the invention has been described and illustrated with reference to certain preferred embodiments thereof, those skilled in the art will appreciate that various modifications, changes, omissions and substitutions can be made without departing from the spirit of the invention. It is intended, therefore, that the invention be limited only by the scope of the following claims.

What is claimed is:

1. An acronycine compound of the formula:

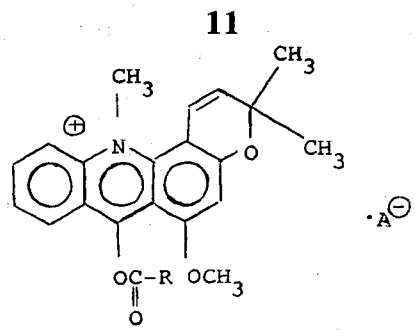

wherein R is straight or branched chain lower alkyl or halo alkyl having from 1 to 8 carbon atoms or phenyl or naphthyl, alkaryl or aralkyl wherein the aryl thereof is phenyl or naphthyl and the alkyl thereof is as above defined and A is a pharmaceutically acceptable anion of a strong quaternizing acid.

2. The acronycine compound as defined by claim 1 wherein said anion of a strong quaternizing acid is selected from the group consisting of perchlorate, chloride, sulfate, phosphate, bromide and methanesulfonate.

3. An intermolecular complex of (1) an acronycinium salt of the formula:

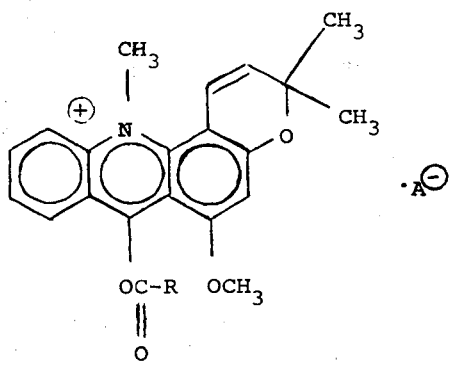

wherein R is straight or branched chain lower alkyl or halo alkyl having from 1 to 8 carbon atoms or phenyl or naphthyl, alkaryl or aralkyl wherein the aryl thereof is phenyl or naphthyl and the alkyl thereof is as above defined and A is a pharmaceutically acceptable anion of a strong quaternizing acid, and (2) a complexing agent selected from the group consisting of gentisic acid, gamma-resorcylic acid, p-hydroxycinnamic acid, 2-furoic acid, m-hydroxycinnamic acid, 3,4-dimethylcinnamic acid, 3-methyl gentisic acid and the pharmaceutically acceptable non-radioactive alkali metal salts thereof.

4. The intermolecular complex as defined by claim 3 wherein said anion of a strong quaternizing acid is selected from the group consisting of perchlorate, chloride, sulfate, phosphate, bromide and methanesulfonate.

5. The intermolecular complex as defined by claim 3, wherein said complexing agent is sodium gentisate.

6. The intermolecular complex as defined by claim 3 consisting of acronycinium perchlorate-gamma-resorcyclic acid complex.

7. The intermolecular complex as defined by claim 3 consisting of acronycinium chloride-cinnamic acid complex.

8. The acronycine compound as defined by claim 1, wherein R is straight or branched chain lower alkyl or halo-lower alkyl having from 1 to 8 carbon atoms.

9. The acronycine compound as defined by claim 8, wherein the ester group $RCO_2$ is selected from the group consisting of acetate, propionate, isobutyrate, pivalate and trifluoroacetate.

10. The complexation product as defined by claim 3, consisting of acetylacronycinium perchlorate-sodium gentisate.

* * * * *